(12) United States Patent
Welten (10) Patent No.: US 6,652,549 B1
(45) Date of Patent: Nov. 25, 2003

(54) DEVICE FOR STRIPPING VEINS (75) Inventor: Robertus Johannes Theodorus Josephus Welten, Heerlen (NL)

(73) Assignee: Le Maitre Vascular, Inc., Burlington, MA (US)

( * ) Notice: Subject to any disclaimer, the term of this patent is extended or adjusted under 35 U.S.C. 154(b) by 0 days.

(21) Appl. No.: 09/889,675

(22) PCT Filed: Jan. 19, 2000

(86) PCT No.: PCT/NL00/00039

§ 371 (c)(1),
(2), (4) Date: Oct. 16, 2001

(87) PCT Pub. No.: WO00/42918

PCT Pub. Date: Jul. 27, 2000

(30) Foreign Application Priority Data

Jan. 19, 1999 (NL) .......................................... 1011063

(51) Int. Cl.[7] ............................................. A61B 17/32
(52) U.S. Cl. ........................ 606/159; 606/167; 606/170
(58) Field of Search ................. 606/167, 170, 606/159; 604/22; 128/898

(56) References Cited

U.S. PATENT DOCUMENTS

| | | | | | |
|---|---|---|---|---|---|
| 3,568,677 A | * | 3/1971 | Nolan et al. | ................. | 606/159 |
| 5,320,634 A | * | 6/1994 | Vigil et al. | ................. | 606/159 |
| 5,667,480 A | * | 9/1997 | Knight et al. | ............... | 600/210 |
| 6,030,396 A | * | 2/2000 | Samuels | .................... | 606/159 |
| 6,193,653 B1 | * | 2/2001 | Evans et al. | ................ | 600/210 |
| 6,398,798 B2 | * | 6/2002 | Selmon et al. | .............. | 606/159 |

FOREIGN PATENT DOCUMENTS

| | | |
|---|---|---|
| EP | 0 533 320 A2 | 3/1993 |
| EP | 0 551 707 A1 | 7/1993 |

\* cited by examiner

Primary Examiner—Michael J. Milano
Assistant Examiner—Paul A Roberts
(74) Attorney, Agent, or Firm—Young & Thompson (57) ABSTRACT

A device for stripping veins (5), includes a catheter element (9) which extends in the axial direction from a proximal end to a distal end (10), wherein the distal end (10) is provided with cutting devices, with cutting elements (24), which are movable between a first or neutral position, in which the cutting elements (24) extend essentially in the axial direction of the catheter element (9), and a second or working position, in which the cutting elements (24) are directed outwards with respect to the catheter element (9).

16 Claims, 5 Drawing Sheets

DEVICE FOR STRIPPING VEINS

FIELD OF THE INVENTION

The present invention relates to a device for stripping veins, comprising a catheter element which extends in the axial direction from a proximal end to a distal end. The device according to the present invention is suitable for removing veins and in particular is suitable for removing the vena saphena magna. This vena saphena magna is also referred to as VSM.

BACKGROUND OF THE INVENTION

In man the blood circulation consists of arteries which supply blood and veins which carry blood away. Valves, which act as a non-return valve, are attached to the inside wall of these veins. Every time a person moves his or her body the veins are contracted somewhat by the flexing of the muscles, As a result of this contracting effect the blood is fed via the "non-return valves" in the direction of the heart.

The venous system in the legs consists of a deep venous system and a surface system In the deep venous system the vena femorales communus in particular is important. In the surface system the VSM and the vena saphena para (VSP) are the most important veins. The surface system is in the subcutaneous fatty tissue.

In medical science it is known that an increase in the diameter of the veins or damage to the valves in the veins results in insufficient functioning of the venous valves. If these valves do not function adequately, the blood pressure in the veins will increase and as a result the veins will expand. Moreover, the veins start to knot and is visible through the skin. This abnormality is also referred to as varicosis or "varicose veins".

In order to prevent complications in the case of varicosis the VSM must be removed from the human body. This surgical treatment is also referred to as "stripping" or "exeresis", After the removal or stripping of the VSM the outflow of the venous blood from the legs takes place through the deep venous system. Usually the capacity of the deep venous system is sufficient to ensure a good outflow, It is possible to remove the entire VSM, from the ankle to the groin. Such a treatment is also referred to as a "long strip". It is also possible to remove part of the VSM, that is to say from the knee to the groin. Such a treatment is also referred to as "short stripping". Carrying out a so-called short strip usually yields better results and this method is therefore currently standard in medical science. One of the major advantages is that the risk of damage to the nervus saphenus is much lower than in the case of a long strip.

The nervus saphenus nerve runs essentially parallel to We VSM in the leg. This nervus saphenus can become damaged when removing the VSM. Therefore it is advantageous if that section of the VSM from the knee to the ankle remains behind in the leg.

In the state of the art it is customary to remove the VSM with the aid of a catheter. This catheter is also referred to as the "stripper". This catheter is formed by a long, in, flexible element that is introduced into the VSM from the groin. To this end an initial incision is made in the skin at the location of the groin. The catheter is inserted in the VSM until the distal end reaches the knee. A second incision is made at the location of the knee and the VSM, with. the distal end of the catheter therein, is partially pulled out of the body. The lower section, or the supplying section of the VSM, is ligated. That is to say: closed off by knotting with for example, a wire and left behind in the leg. The upper section of the VSM, or the discharging section, that runs from the knee to the groin is attached to the catheter with the aid of a ligature or a wire. A cap, the so-called strip head, is then fitted on the end of the catheter, which cap ensures that the catheter Yes a relatively broad cross-section close to the end.

The catheter is then pulled out of the human body from the groin end, During this operation the VSM is removed from the body with the catheter. During this operation the cap fitted on the end of the catheter serves as a stop which ensures that the VSM is pushed forward from the knee end in the direction of the groin.

This known method and the instruments used for this method have a number of disadvantages. Firstly, an incision has to be made at the location of the knee. This incision must be sufficiently large for the cap which is fitted on the end of the catheter to be inserted through the opening. For proper operation of the stop function the cap usually has a diameter of 12–16 mm. This means that the incision has to be made relatively large. Many patients find it a disadvantage from the cosmetic standpoint that a scar will remain on the leg at the location of the knee. Secondly, it is disadvantageous that the cap which is fitted on the end of the catheter acts as a propulsion element. The VSM will accumulate as a plug in front of the cap when the catheter is pulled out of the human body. This plug will become increasingly large as the end of the catheter approaches the groin, This means that a relatively wide subcutaneous channel is drawn through the patient's thigh. This wide channel can cause internal damage and complications. Finally, searching for, exposing and tying off the VSM at the location of the knee increases the risk of injury to the nervus saphenus.

SUMMARY OF THE INVENTION

The aim of the present invention is to provide a device with the aid of which a vein, and in particular the section of the VSM, can be removed from the human body, the device being designed such that it is not necessary to make an incision in the skin at the location of the knee. What must be achieved t this device is that the channel rains behind in the leg after removal of the VSM, or the subcutaneous channel, is as small as possible.

Said aim is achieved in the present invention in that the distal end is provided with cutting means, with cutting elements, which are movable between a first or neutral position, in which the cutting elements extend essentially in the axial direction of the catheter element, and a second or working position, in which the cutting elements are directed outwards with respect to the catheter element.

With the aid of the device according to the present invention it is possible to allow the cutting elements to act endovascularly (from the inside of the venous vessel) on the vein wall. This means that the second incision, which generally speaking was needed to search for and cut through the VSM, becomes superfluous.

According to the present invention it is advantageous that the catheter element is provided with guide means for guiding the cutting elements from the first position into the second position.

In this context it is possible that the cutting means comprise a base body that is slidably attached to the catheter element, the cutting elements being hingeably connected to said base body. In this context it is advantageous that the guide means are formed by a thickening at the distal end of the catheter element, it being possible to move the base body from the first position in the axial direction to the distal end of the catheter element into the second position, the thickening being forced between the cutting elements during this movement the various features being such that in the second position the cutting elements are directed essentially outwards with respect to the catheter element.

In practice it will be possible to move the catheter, at the distal end thereof provided with the cutting elements, backwards in the VSM from the groin to the knee, The VSM can then be joined to the catheter inserted in the VSM with the aid of a subcutaneous ligature. This join is produced with the aid of a loop made in the life. This ligature is deliberately kept relatively long and positioned on the groin side of the cutting elements.

Traction or tensile force can then be exerted on the catheter, whilst the cutting elements are essentially held in place in the VSM. The cutting elements are held in place by exert traction in the opposite direction with the aid of the Ligature. What is achieved by this means is that the cutting element is moved from the first, neutral position into the cutting position. In said cutting position the cutting elements will at least partially weaken the wall of the VSM from the inside, for example by partially cutting tough or perforating the wall.

Furthermore, it is possible for the cutting means to be arranged such that they are movable in the axial direction towards the distal end of the catheter element from the second position into a third position, wherein in the third position the thickening is taken up in a space which is enclosed by the cutting elements and the base body, respectively. By applying further traction in the direction of the di end of the catheter element with the aid of the ligature, the cutting elements can be brought into a second neutral position. In said second neutral position the cutting elements will again extend essentially in the axial direction along the catheter element. On further traction, the VSM will tear off at the location of the perforations or cuts made. The upper section of the VSM will be removed from the leg with the catheter, The lower section, or supplying section, of the VSM is not tied off but is taken care of by external compression.

Reference has been made above to traction which is exerted with the aid of the catheter, whilst traction in the opposing direction is exerted with the aid of the ligature. The same effect can, of course, also be achieved by using the ligature as a stop, traction being exerted solely with the aid of the catheter.

Because the catheter according to the present invention will have a relatively small diameter, even when the cutting element has been fixed to the distal end, it is possible to remove the VSM by invagination. In this procedure the lumen of the VSM is used as guide channel The vessel is turned inside out during the removal thereof.

A relatively long ligature is used when attaching the wall of the vein to the catheter, at the location of the cutting element. During removal of the catheter this ligature can be used to exert traction on the distal end of the catheter element, which traction is in the opposite direction to the traction on the catheter element itself. Because the traction on the catheter element and the counter-traction can be regulated well, the catheter can be pulled out of the human body in a controlled manner.

According to a further embodiment it is possible for the guide means to be formed by auxiliary arms which are hingeably joined at one end to the distal end of the cutting elements and at the other end to the distal end of the catheter element. With the aid of the relatively long wire the cutting elements can again be moved from a first neutral position via a cutting position into a second neutral position, guiding of the cutting elements being carried out by the auxiliary arms.

According to a further embodiment it is possible to construct the catheter element with two bodies. With this arrangement it is possible for the catheter element to comprise an inner catheter body and an outer catheter body arranged around the inner body, wherein the inner catheter body is movable in the axial direction with respect to the outer catheter body, whilst the inner catheter body is provided at the distal end thereof with one or more cutting elements, and wherein the outer catheter body is provided at the distal end thereof with guide means, and the inner body is movable relative to the outer body from a first position in which the cutting elements are essentially enclosed by the guide means into a second position in which the cutting elements have been moved essentially in the radial direction out of the guide means.

It is also possible for the catheter element to be provided at the end thereof with one or more cutting elements, wherein said cutting elements are mounted on either side of or on an inflatable body, the various features being such that the cutting elements can be moved radially outwards by inflating the inflatable element.

For the device according to the present invention to function well it is advantageous that the device has a length of preferably 600 to 1000 mm, :more particularly of 600 to 750 mm and more preferentially of 600 to 700 mm.

Use of the device according to the present invention has a number of advantages. Firstly, the number of actions tat have to be performed in order to remove the upper section of the VSM is relatively limited. This means that the operation can be carried out quickly and that the operating theatre facilities can be better utilized Secondly, the number of disposable instruments is limited because the distal incision at the location of the knee, ligating the VSM and closing the distal incision become superfluous.

In view of the abovementioned advantages, it is advantageous for the device according to the present invention to be packed as a kit.

It is possible for a kit comprising the installation according to the invention and a surgical wire, which is provided at the end thereof with a prefitted cutting needle, to be packed sterile as a whole in a container. It is possible for the kit also to contain a surgical knife. In this context it is possible for the surgical wire to have a length of 1000 to 1600 mm, preferably 1200 to 1400 mm and most preferentially 1300 mm.

Sterile packaging of the abovementioned kit has the advantage that operating theatre logistics can be simplified appreciably.

BRIEF DESCRIPTION OF THE DRAWINGS

The present invention will be further explained with reference to the following figures, in which.

DETAILED DESCRIPTION OF THE INVENTION

Figure 1:
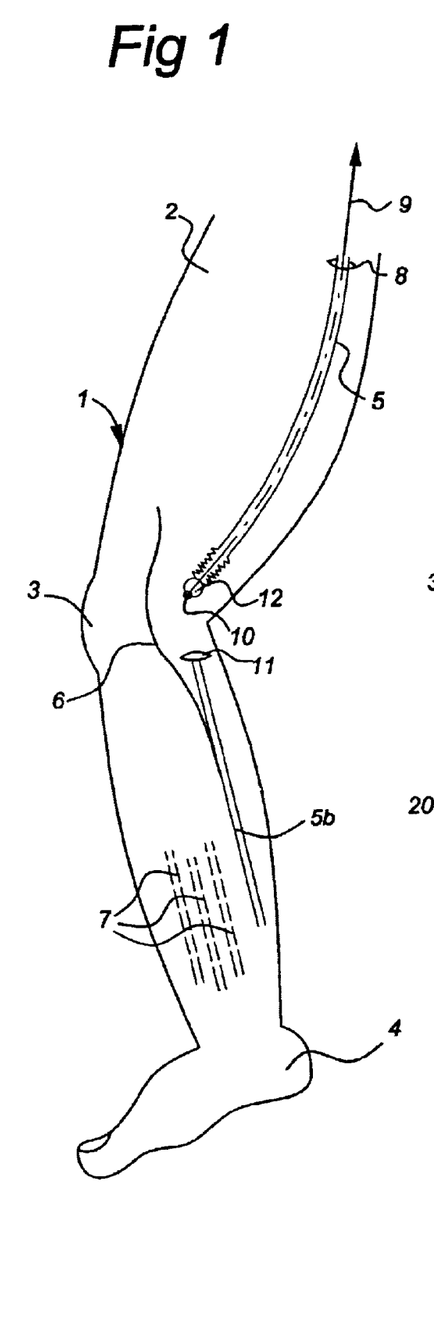
FIG. 1 shows, diagrammatically, the patient's leg with a short strip of the VSM being performed with the aid of a stripper according to the prior art.

FIG. 1 shows removal of the VSM in accordance with the state of the art. The leg 1 of a patient is shown diagrammatically in FIG. 1. The leg has a groin 2, a knee 3 and a foot 4. The upper section of the VSM 5 extends from the knee 3 to the groin 2. The lower section of the VSM 5b extends from the ankle to the knee 3. Below the knee 3 the nervus saphenus 6 runs essentially parallel to the VSM 5b. The deep venous system 7 is also indicated diagrammatically in the lower leg. When the VSM 5 is removed from the leg the deep venous system will take over the transport of blood from the foot towards the groin 2.

For removal of the upper or cranial section of the VSM 5, a first incision 8 is made in the fold of the groin. The cross and the VSM are sought via this incision 8. Initially a so-called crossectomy is carried out. This means that all side branches of the VSM which open into the deep system are cut through and ligated, Following this crossectomy, the catheter element 9 is inserted via a venotomy in the VSM 5 through the vein in the direction of the knee 3.

At the end of the catheter element 9 there is a thickening 10. When this thickening 10 has reached the knee, a second incision 11 is made in the leg at the location of the knee 3. The VSM 5, 5b is then guided out of the leg at the location of a second incision 11 and cut through. The lower section of the VSM 5b is ligated.

A knob 12 is then placed on the thickening 10 at the end of the catheter element 9. The free end of the upper section of the VSM 5 is then tied to the end of the catheter element 9 with the aid of a ligature. The catheter element 9 is then pulled out of the leg in the direction of the groin. As a result of this movement, the VSM will be pulled out of the body with the catheter element 9. The knob 12 at the end of the catheter element 9 serves as a stop element during this procedure. The VSM 5 will start to roll up somewhat when the catheter element 9 is pulled out and will collect as a plug against the knob 12, FIG. 1 shows the situation where the catheter element 9 has already been pulled some distance out of the thigh.

As already mentioned in the preamble, the method described above has a number of significant disadvantages. Firstly, a second incision 11 must be made in the leg at the location of the knee 3. Especially from the cosmetic standpoint, this incision is undesirable, Moreover, this incision must be relatively large because this incision is matched to the dimensions of the knob 12 which is fitted on the end of the catheter element 9. In order to function well this knob has a diameter which is usually 12 to 16 mm. A second disadvantage is the fact that the VSM 5 collects as a plug in front of the knob 12 when the catheter element 9 is pulled out. This means that the size of the channel that is drawn through the thigh when remove the VSM is determined by the size of the plug which forms in front of said knob 12. The larger this plug, the larger will be the channel that is drawn through the thigh.

Figure 2:
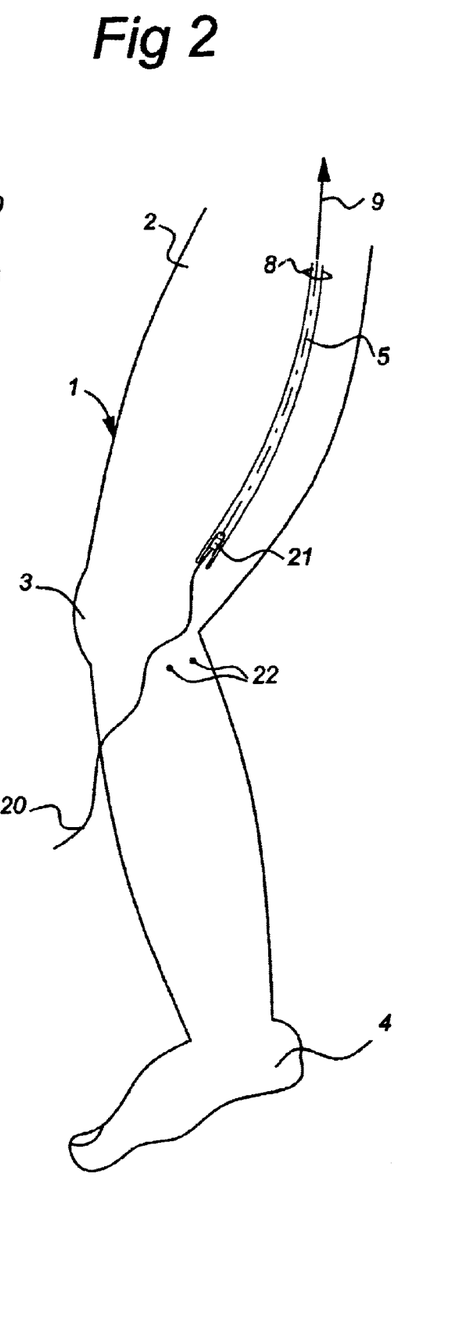
FIG. 2 shows, diagrammatically, a patient's leg with a short strip of the VSM being performed with the aid of the catheter according to the present invention.

FIG. 2 shows a patient's leg 1 where the upper section of the VSM 5 is being removed with the aid of the device according to the present invention.

Once again a first incision 8 has been made in the leg 1 at the location of the groin 2. The catheter element 9 has been moved through his incision 8 in the direction of the knee 3. As soon as the end of the catheter element 9 has reached the knee, and can be felt there through the skin, a physician will attach the end of the catheter element 9 to the VSM 5, 5b with the aid of a wire 20. An atraumatic wire with a cutting needle of triangular cross-section can be used for attaching the end of the catheter element 9 to the VSM 5, 5b. It is advantageous if the wire is made fairly long, with, for example, a length of 100 to 160 cm.

In order to be able to attach the surgical wire 20 to the distal end of the catheter element 9, the skin must be perforated with the needle. It is clear that the damage caused by this means is of a minimal invasive nature compared with the scar that is produced with the method according to the prior art.

When the end of the catheter element 9 has been attached to the VSM, the upper section of the VSM 5 can not yet be removed from the leg 1 because the VSM 5, 5b has not yet been cut through.

To ensure tat the VSM 5, 5b is cut through at the ankle end of the catheter, the vein wall can be damaged, punctured or cut through just below the join to the end of the catheter element 9 with the aid of a needle inserted through the skin. However, this causes damage to the patient's skin at the location of the knee, One of the aims of the present invention is, precisely, to restrict damage to the skin of the knee to a minimum. Secondly, perforating or puncturing the wall of the VSM 5, 5b is a blind procedure that must be carried out by feel Since the nervus saphenus runs in the immediate vicinity of the VSM 5, 5b in this region there is a real risk that the nervus saphenus will also be damaged or cut through during this procedure, As a result a temporary or even permanent loss of feeling or impaired feeling in the lower leg can arise at the end of an operation.

To avoid these disadvantages, the present invention provides for cutting means 21, at the end of the catheter element 9, which are at least able to damage the wall of the VSM 5, 5b from the inside (endovascularly). It is clear that the wall of the VSM does not have to be cut through completely. When there is an indication for stripping the VSM the tatter will be insufficient and thus weakened, By damaging the vein wall at one or more points the vein will be able to tear free relatively easily on applying an axial force.

In an advantageous embodiment the cutting means 21 at the end of the catheter element 9 are so constructed that when an axial force is exerted in the direction of the distal end of the catheter element 9 by means of the relatively long wire 20 with which the wall of the VSM 5, 5b has been attached to the catheter element 9, the cutting means 21 will move along the catheter element in the axial direction, Via an extreme, cutting, position, the cutting elements will move back a into a neutral position, The precise functioning of the cutting means 21 according to the present invention will be further explained with reference to the following figures.

When the wall of the VSM has been cut through or weakened with the aid of the cutting means 21 at the end of the catheter element 9, the cranial section of the VSM 5 can be pulled out of the leg with the aid of the catheter element 9. As a result of the presence of the relatively long wire 20, a force can be exerted on the catheter element 9, in the direction of the distal end of the catheter element 9, when pulling out the catheter element 9. As a result of the presence of this 'opposing force', the catheter element 9 can be pulled out of the leg gradually, that is to say in a controlled manner. If needed, the catheter element 9 can also be pulled back into the leg to some extent Backward and forward movement of the catheter element 9 can, for example, be needed when passing by side branches of the VSM 5.

It can also be seen from FIG. 2 that according to the present invention the VSM 5 is removed via an invaginating method. This means that the lumen of the VSM 5 is used as guide for that section of the vein that has already been pulled out from its subcutaneous bed. This means, inter alia, that the diameter of the subcutaneous channel that is drawn in the leg is not determined by the accumulation of the outer wall of the VSM 5 against a retaining element, but that the size of said channel is essentially determined by the diameter of the cutting means 21 which have been attached to the end of the catheter element 9.

The length of the catheter element according to the present invention is preferably 60 to 100 cm, more particularly 60 to 75 cm and most preferentially approximately 60 cm The length of the catheter element must be sufficient to bridge the distance from a patent's groin to the knee. The external dimension of the catheter element can be approximately 2 to 2.5 mm. The difference in external diameter between the cutting means at the end of the catheter element and the catheter element itself must be as large as possible to guarantee secure joining of the outer wall of the VSM to the catheter element. The catheter element must be of such construction that it is able to withstand a load of 400 Newton.

The catheter element is preferably sterilised with the aid of ethylene. This imposes the requirement that the material of the catheter must be heat resistant up to temperatures of approximately 140° C.

It is possible to provide the catheter element with indicator lines over the length thereof. These indicator lines or markings can, for example, be made on the catheter element every 10 cm. With the aid of these markings a surgeon is able to see what length of the VSM has already been pulled out of the body.

The diameter of the cutting means, which are attached to the end of the catheter element, is preferably 4–10 mm, more preferentially 5–8 mm and most preferentially 6 mm. Normally it is not possible to insert a catheter into a healthy VSM counter to the valve direction. In the case of a 'diseased' VSM, such as exists in the case of varicose veins, this is possible since in this case the valves are insufficient and are not able to offer any resistance.

As has already been stated above with reference to FIG. 2, the end of the catheter element 9 is attached to the wall of the VSM 5, 5b with the aid of a ligature. This wire must be relatively strong because it must be able to be used to exert counter-force on the catheter element itself. The length can be chosen between, for example, 100 and 160 cm. As a result of this length it is possible to move the catheter element 9 backwards and forwards through the VSM after ligation, if desired. For attaching the catheter element 9 to the wall of the VSM 5, the atraumatic ligature can be provided with a cutting, triangular needle.

It is advantageous to pack the catheter element according to the present invention, provided with the cutting means, together with the needle and wire and an operating knife as a sterile kit. Operation theatre logistics can be substantially simplified by putting together this "operation kit".

When preparing for an operation according to the state of the art a relatively large number of disposable instruments must be held in stock in the operating theatre complex. For instance, there is a need for a first cutting element for making a first incision; frequently a second, smaller cutting element for making a second incision; sutures for ligating the lower section of the VSM 5b which has been cut free and for ligating the side branches of the VSM after the crossectomy; a suture for attaching the end of the catheter element to the upper section of the VSM; sutures for closing the first and the second incision and also the actual catheter element or catheter elements itself/themselves depending on whether a single or a double operation is being carried out. By putting together the 'kit' as stated above, keeping the requisite components in stock can be limited to keeping a number of operating kits according to the present invention in stock.

Figure 3:
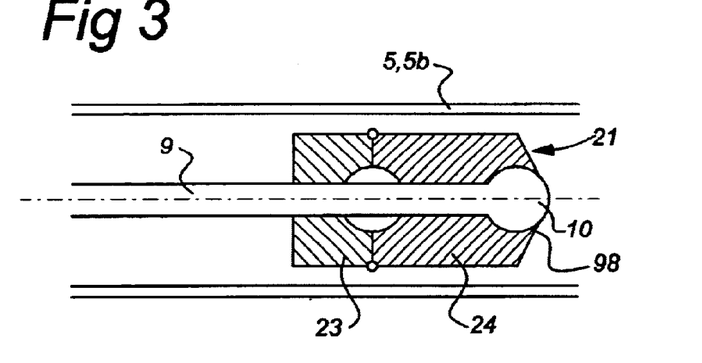
FIGS. 3, 4 and 5 indicate various positions of the cutting means according to a first embodiment according to the present invention.
Figure 4:
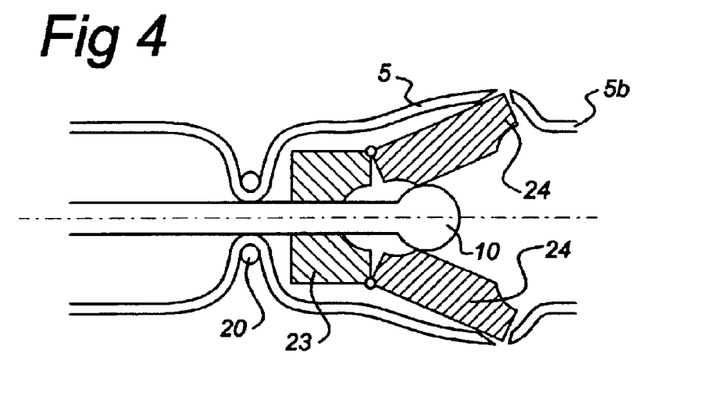
Figure 5:
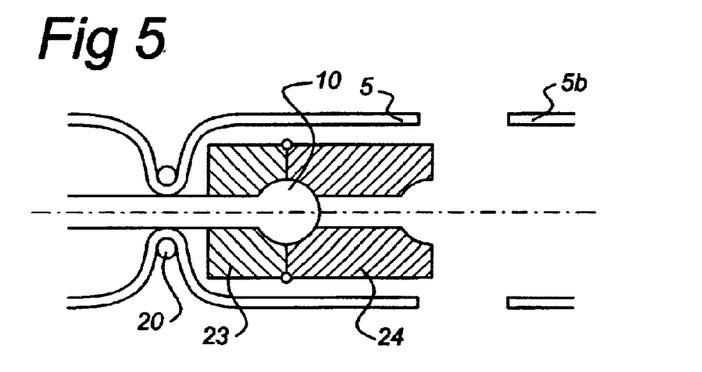

FIGS. 3, 4 and 5 show a first embodiment of the cutting means 21 with the aid of which the all of the VSM 5, 5b can be perforated or cut through.

FIG. 3 shows the case where the catheter element 9, with the cutting means 21 at the end thereof, has been placed in the VSM 5, 5b. When the end of the catheter element 9 is at the location of the knee 3, the wall of the VSM 5, 5b is attached to the outer surface of the catheter element 9 with the aid of a relatively long wire 20. The long wire 20 is shown diagrammatically in FIG. 4.

The cutting means 21 according to the illustrative embodiment shown in FIGS. 3, 4 and 5 comprise an annular base body 23 to which one or more cutting elements 24 are hingeably joined. Said cutting elements 24 can be moved from a neutral, or first, position which is shown in FIG. 3 into a working or cutting position which is shown in FIG. 4. The cutting elements 24 cm be moved from the neutral, first position into the working position with the aid of the wire 20. With the aid of said wire 20, an axial force can be exerted in the direction of the distal end of the catheter element 9. With the aid of this axial force the thicker section 10 at the end of the catheter element 9 is forced between the cutting elements 24 located next to one another. This forces said cutting elements 24 radially outwards, the cutting elements being able to execute a cutting movement on the wall of the VSM 5, 5b. The wall of the VSM 5, 5b can be weakened, damaged or cut through completely during this movement. As a result the VSM is separated into a section 5 that leads to the groin and a section 5b that comes from the ankle.

When, starting from the working position which is shown in FIG. 4, further axial force is exerted on the cutting means 21 in the direction of the distal end of the catheter element 9 a second neutral position can be reached, which is shown in FIG. 5. In this second neutral position the thicker section 10 is taken up in a recess which is enclosed between the base body 23 and the various cutting elements 24. In this neutral position the cutting elements 24 have once again moved somewhat radially inwards. The catheter element 9 with the cutting means 21 thereon can then be pulled out of the body without the cutting elements 24 executing a further cutting movement on the vein or on surrounding tissue.

It can be seen from a comparison of FIGS. 3 and 4 that the cutting elements 24 according to FIG. 3 are provided with an extension 98 at the distal end thereof. In use this extension 98 can prevent the cutting means 21 from shifting relative to the catheter element 9 when the catheter is inserted in the VSM. It is, of course, also possible to allow these extensions 98 to continue even further in the direction of the distal end of the catheter element 9.

Figure 6:
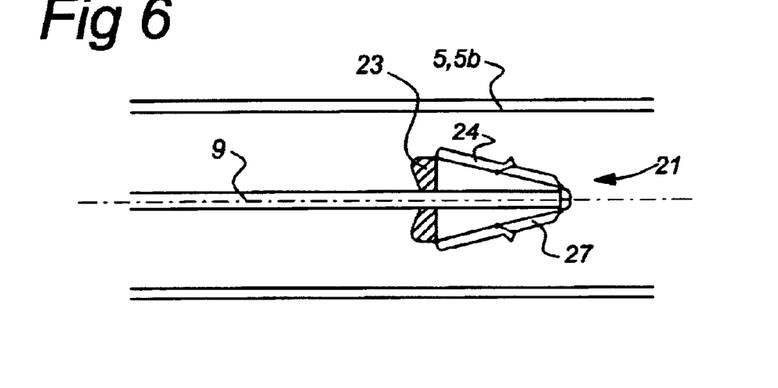
FIGS. 6, 7 and 8 show the various positions of the cutting means according to a second embodiment of the present invention.
Figure 7:
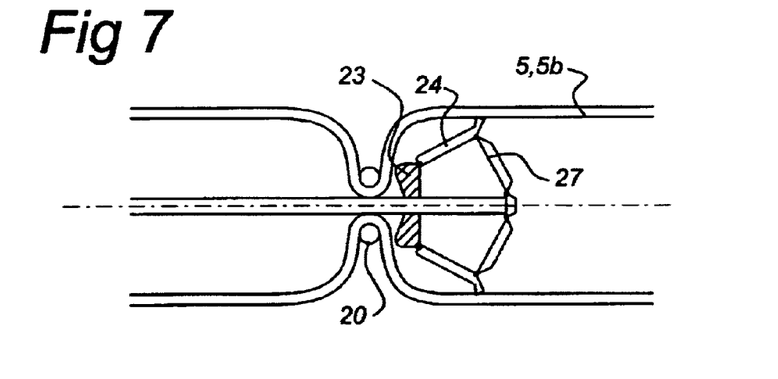
Figure 8:
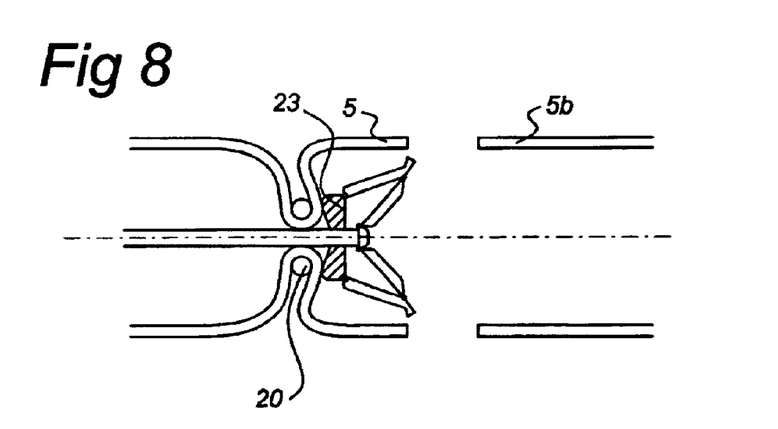

The cutting means which are shown in FIGS. 3, 4 and 5 can also be constructed in various other ways. A further embodiment is shown in FIGS. 6, 7 and 8. In this case as well, the cutting means 21 can be removed via a first neutral position which is shown in FIG. 6, via a cutting position which is shown in FIG. 7, into a second neutral position which is shown in FIG. 8.

It also possible to construct the catheter element from FIGS. 3, 4 and 5, or 6, 7 and 8, with the aid of a first or outer catheter element 90, which forms a whole with the base body 23, and a second or inner catheter element 91.

Figure 9A:
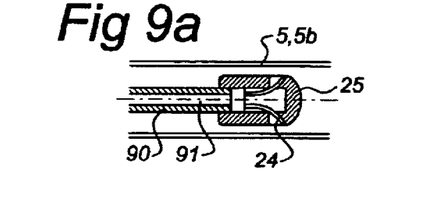
FIGS. 9a, 9b and 9c show three positions of a third embodiment of the cutting means of the catheter according to the present invention.
Figure 9B:
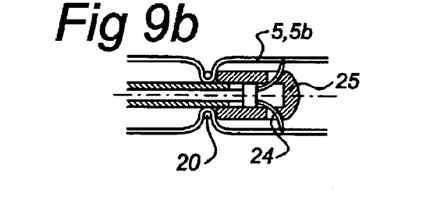
Figure 9C:
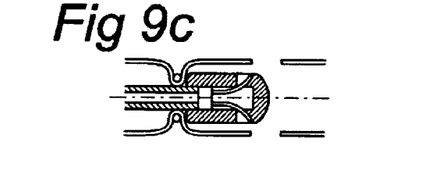

A further possible embodiment thereof is shown in FIGS. 9a, 9b and 9c. A first neutral position is shown in FIG. 9a. The inner catheter element 91, to the end of which cutting elements 24 have been attached, has been pulled into the outer catheter element 90 to such an extent that the cutting elements are essentially enclosed by a covering 25 that at the end is joined to the outer catheter element 90. By now moving the inner catheter element 91 in the distal direction from the outer catheter element 90 the cutting elements 24 are forced radially outwards, This is shown in FIG. 9b. In the position shown in FIG. 9b the cutting elements 24 will execute a cutting movement on the wall of the VSM 5, 5b. After executing this cutting operation, the cutting elements 24 can be pulled back into the covering 25 by pulling the inner catheter element 91 in the proximal direction relative to the outer catheter element 90.

The various inner 91 and outer 90 catheter elements must be so constructed that the position of the cutting means (neutral or working position) at the distal end of the catheter elements must be recognisable from the proximal end of the catheter elements 90, 91. This means, for example, that hand grips are arranged on the proximal end of the elements, the mutual position of the hand grips indicating the position of the cutting means.

Figure 10A:
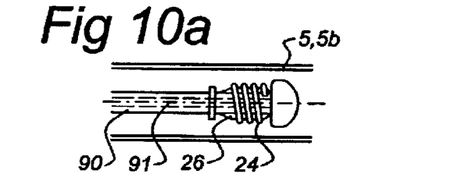
FIGS. 10a, 10b and 10c show three positions of a fourth embodiment of the cutting means of the catheter according to the present invention.
Figure 10B:
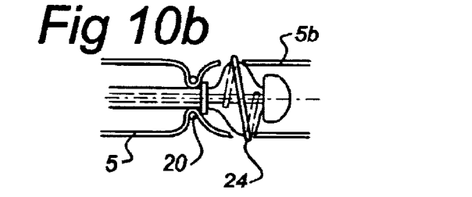
Figure 10C:
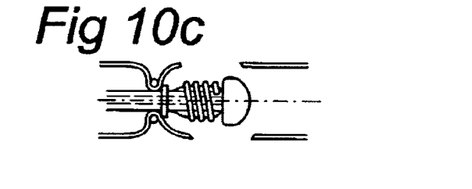

If use is made of an inner and an outer catheter element, one of the two elements can also be used for inflating or pumping up a balloon or a similar element with the aid of a fluid. This is shown inter alia in FIGS. 10, 11 and 12. FIGS. 10a, 10b and 10c show a catheter element where an inflatable element 26 is attached to the end thereof. A cutting element 24 is arranged in spiral form on the outer surface of the inflatable element 26. When the catheter element has been placed in the correct position and the outer wall of the VSM has been attached to the catheter element, the inflatable element 26 can be inflated with the aid of a line that extends to the proximal section of the catheter element. The cutting elements or the cutting element 24 are/is forced radially outwards by this means. As a result a cutting movement can be executed on the wall of the VSM 5, 5b. After executing the cutting operation, the cutting means 24 can be moved back into a neutral position by allowing the inflatable element 26 to empty.

Figure 11A:
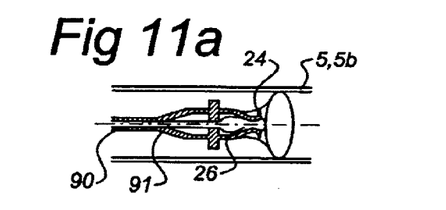
FIGS. 11a, 11b and 11c show three positions of a fifth embodiment of the cutting means of the catheter according to the present invention.
Figure 11B:
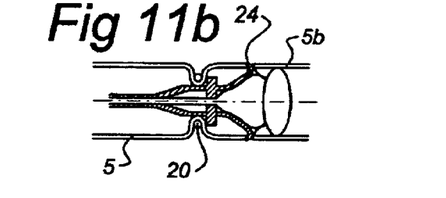
Figure 11C:
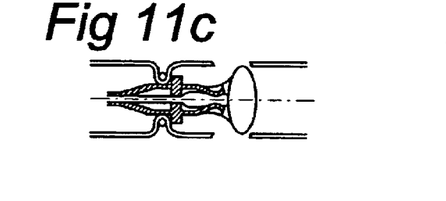

Something similar applies in the case of the embodiment which is shown in FIGS. 11a, 11b and 11c. The embodiment which is shown in FIGS. 11a, 11b and 11c also has an outer and an inner element 90 and 91, respectively. By inflating an inflatable element 26, which in this case is arranged between two or more cutting elements 24, said elements can be moved radially outwards, as is shown in FIG. 11b, and during this movement execute a cutting operation. At the end of this cutting operation, the inflatable element 26 can be emptied again, with the result that he cutting elements 24 will move inwards into the neutral position as is shown in FIG. 11c.

Figure 12A:
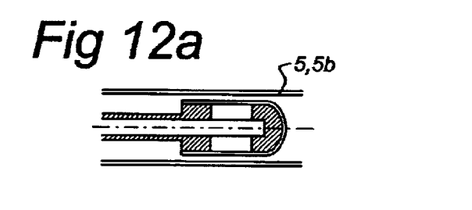
FIGS. 12a, 12b and 12c show three positions of a sixth embodiment of the cutting means according to the present invention.
Figure 12B:
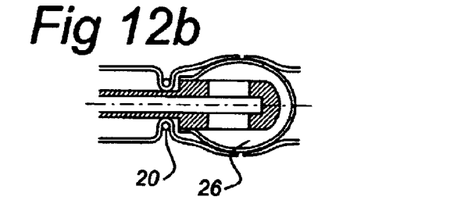
Figure 12C:
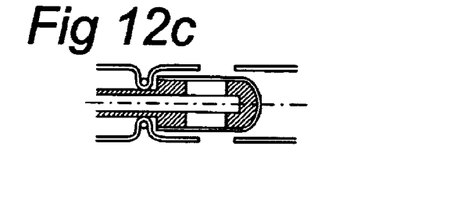

Because the VSM is only removed from patients whose VSM is insufficient it can suffice to exert a radial force on the wall of the VSM 5, 5b. This means that it can suffice to exert a radial force on the wall of the VSM with the aid of an inflatable element 26 which has no additional cutting elements arranged on the outside. This is shown in FIGS. 12a, 12b and 12c.

Figure 13A:
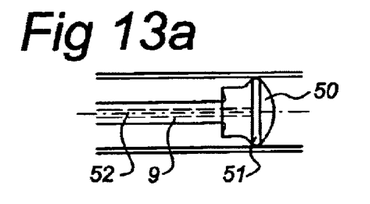
FIGS. 13a, 13b and 13c show three positions of a seventh embodiment of the cutting means according to the present invention.
Figure 13B:
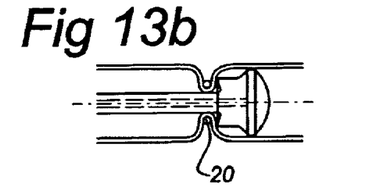
Figure 13C:
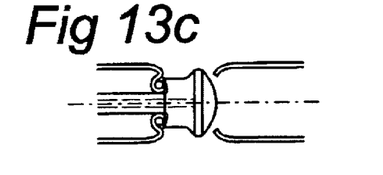

In addition to the embodiments discussed above, yet further embodiments of the catheter element according to the present invention are possible. These further embodiments are shown in FIGS. 13–16. FIG. 13a shows a catheter element according to the present invention where the catheter element ends in a thickening or knob 50. Conducting means 51 are provided on the outside thereof. Conducting means 52, for example for conducting current, are provided in the catheter element 9. When the catheter element has been fixed in the correct position with the aid of the wire 20, as is shown in FIG. 13b, a current can be applied to the means 51 with the aid of the conducting means 52. The wall of the VSM can, as it were, be "burnt through" with the aid of this current. After the wall has been weakened or burnt trough the catheter element 9 can be pulled out of the body in a manner corresponding to that already described above.

Figure 14A:
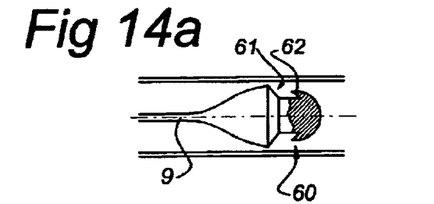
FIGS. 14a, 14b and 14c show three positions of an eighth embodiment of the cutting means according to the present invention.
Figure 14B:
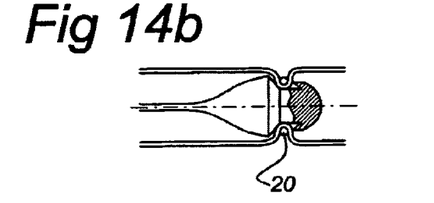
Figure 14C:
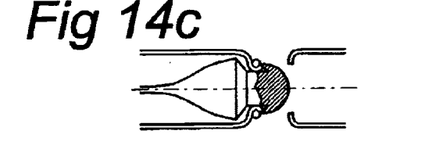

A further possibility is shown in FIGS. 14a, 14b and 14c. FIG. 14a shows a catheter element 9 which opens into an element 60 which has a slot or a channel 61 with sharp or cutting elements 62 at least on one side. After the catheter element 9 has been brought into the correct position with the aid of the wire 20 as is shown in FIG. 14b, a cutting movement can be executed on the wall of the VSM with the aid of the cutting edges 62 by exerting an axial force in the proximal direction. This is shown in FIG. 14c.

Figure 15A:
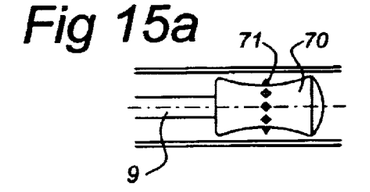
FIGS. 15a, 15b and 15c show three positions of a ninth embodiment of the cutting means according to the present invention.
Figure 15B:
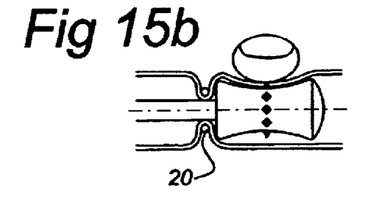
Figure 15C:
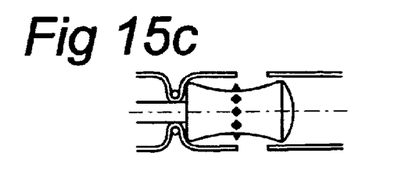

It is also possible to make use of essentially stationary cutting means, for example as is shown in FIGS. 15a, 15b and 15c. When the catheter element 9 has been brought into the correct position with the aid of the wire 20 as is indicated in FIG. 15b, the inside wall of the VSM can be pressed against the cutting elements 71, which are located on the outside wall of the element 70, by exerting external pressure with a finger on the parent's skin. A cutting movement can be effected by this means.

Figure 16A:
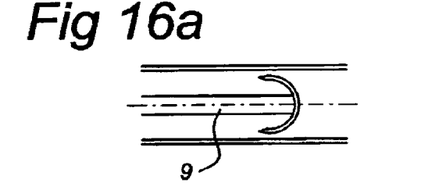
FIGS. 16a, 16b and 16c show three positions of a tenth embodiment of the cutting means according to the present invention.
Figure 16B:
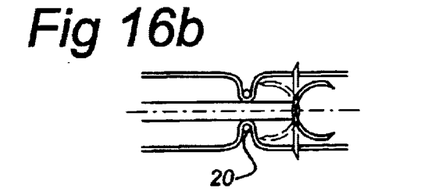
Figure 16C:
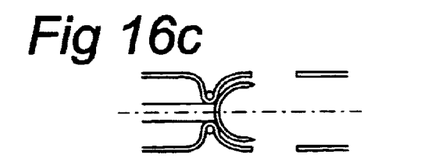

It is also possible to make use of a memory metal. This is shown in FIGS. 16a, 16b and 16c. The catheter element can be brought into a position in the VSM shown in FIG. 16a. When the catheter element 9 has been attached in the correct position in the vessel to the wall of the vessel with the aid of the wire 20 the memory metal can be moved, for example under the action of heat, via a cutting intermediate position, as is shown in FIG. 16b, into, for example, a second neutral position which is shown in FIG. 16c.

It is clear that the cutting means 21 of each of the embodiments shown above either can be moved via a fix net position into a cutting position and then into a second neutral position or can be moved via a first neutral position into a cutting position and then back into the first neutral position thereof.

What is claimed is:

1. A device for stripping a vein, comprising a catheter element having a first or proximal end and a second or distal end, the catheter element at the distal end thereof having vein attachment means to allow the joining of the vein to the catheter element during a stripping procedure, and cutting means for performing at least one of perforating and cutting the vein from the inside, when the vein is attached to the catheter element wherein the vein attachment means have a proximal portion adjacent a distal portion, the external dimension of the distal portion exceeding the respective dimension of the proximal portion of the vein attachment means.

2. The device according to claim 1, wherein the cutting means are movable between a first or neutral position and a second or working position.

3. The device according to claim 2, wherein the catheter element is provided with guide means for guiding the cutting means from the first position into the second position.

4. The device according to claim 2, wherein the cutting means comprise a base body that is slidably attached to the catheter element and cutting elements hingeably connected to said base body.

5. The device according to claim 3, wherein the cutting means comprise a base body that is slidably attached to the catheter element and cutting elements hingeably connected to said base body.

6. The device according to claim 5, wherein the guide means are formed by a thickening at the distal end of the catheter element, wherein the base body is movable from the first position towards the second position in the axial direction of the catheter element, whereby, during this movement the thickening is forced between the cutting elements for guiding the cutting elements essentially radially outwards with respect to the catheter element.

7. The device according to claim 6, wherein the cutting means are arranged such that they are movable in the axial direction towards the distal end of the catheter element from the second position into a third position, wherein in the third position the thickening is taken up in a space which is enclosed by the cutting elements and the base body, respectively.

8. The device according to claim 5, wherein the guide means are formed by auxiliary arms which are hingeably joined at one end to the distal end of the cutting elements and at the other end to the distal end of the catheter element.

9. The device according to claim 2, wherein the external diameter of the cutting means exceeds the diameter of the catheter element in order to provide a thickening for securely fixing the vein attachment means.

10. The device according to claim 9, wherein the vein attachment means comprises a surgical wire serving as a pulling element proximal from the cutting means for exerting on the cutting means an axial force in the direction of the distal end of the catheter element, in order to move the cutting means from the first position towards the second position.

11. The device according to claim 1, wherein the catheter element comprises an inner catheter body and an outer catheter body arranged around the inner body, wherein the inner catheter body is movable in the axial direction with respect to the outer catheter body, wherein the inner catheter body is provided at the distal end thereof with one or more cutting elements comprising the cutting means, and wherein the outer catheter body is provided at the distal end thereof with guide means, and in that the inner body is movable relative to the outer body from a first position in which the cutting elements are essentially enclosed by the guide means into a second position in which the cutting elements have been moved essentially in the radial direction out of the guide means.

12. The device according to claim 1, wherein the catheter element is provided at the distal end thereof with one or more cutting elements comprising the cutting means, wherein said cutting elements are mounted on either side of or on an inflatable body, such that the cutting elements can be moved radially outwards by inflating the inflatable body.

13. The device according to claim 1, wherein the device has a length of 600 to 1000 mm.

14. A kit comprising the device according to claim 1 and wherein the vein attachment means comprises a surgical wire provided at the end thereof with a pre-fitted cutting needle, the kit being packed sterile as a whole in a container.

15. The kit according to claim 14, wherein the kit also comprises a surgical knife.

16. The kit according to claim 14, wherein the surgical wire has a length of 1000 to 1600 mm.

* * * * *